United States Patent [19]

Brants et al.

[11] Patent Number: 6,083,878
[45] Date of Patent: Jul. 4, 2000

[54] USE OF N-(PHOSPHONOMETHYL) GLYCINE AND DERIVATIVES THEREOF

[75] Inventors: Ivo O. Brants, Nieuwerkerken; William Graham, Kortenberg, both of Belgium

[73] Assignee: Monsanto Company, St. Louis, Mo.

[21] Appl. No.: 09/155,429

[22] PCT Filed: Mar. 21, 1997

[86] PCT No.: PCT/EP97/01443

§ 371 Date: May 5, 1999

§ 102(e) Date: May 5, 1999

[87] PCT Pub. No.: WO97/36488

PCT Pub. Date: Oct. 9, 1997

[30] Foreign Application Priority Data

Mar. 29, 1996 [EP] European Pat. Off. ............... 96870036
Jul. 16, 1996 [EP] European Pat. Off. ............... 96870094

[51] Int. Cl.[7] ................................................... A01N 57/02
[52] U.S. Cl. ................................................................ 504/206
[58] Field of Search ............................................. 504/206

[56] References Cited

U.S. PATENT DOCUMENTS

| 3,853,530 | 12/1974 | Franz | 71/76 |
|---|---|---|---|
| 3,988,142 | 10/1976 | Franz | 71/86 |
| 4,025,332 | 5/1977 | Franz | 71/86 |
| 4,840,659 | 6/1989 | Franz | 71/86 |
| 5,464,807 | 11/1995 | Claude et al. | 504/206 |

FOREIGN PATENT DOCUMENTS

| 0 218 571 | 4/1987 | European Pat. Off. . |
|---|---|---|
| 0 293 358 | 11/1988 | European Pat. Off. . |
| 0 441 764 | 8/1991 | European Pat. Off. . |
| 32 00 486 | 7/1983 | Germany . |
| 43 27 056 | 2/1995 | Germany . |
| WO 92/00377 | 1/1992 | WIPO . |
| WO 92/04449 | 3/1992 | WIPO . |
| WO 95/05082 | 2/1995 | WIPO . |
| WO 97/36488 | 9/1997 | WIPO . |

OTHER PUBLICATIONS

Anderson, Wood Powell. Weed Science. p, 136. 1996.

Roundup Ready™ Sugar Beet, I. Brants, et al., pp. 221–222 no date.

"Yield Evaluation of a Glyphosate–tolerant Soybean Line After Treatment with Glyphosate, X. Delannay, et al.," 11–Plant Biochem, vol. 123, 1995, p. 709.

"Development of Glyphosate Tolerant Crops into the Market," B H. Wells (Monsanto Co.), Chemical Abstracts, 5–Agrochemical Bioregulators, vol. 124, No. 7, 1996, p. 494–495.

Effects on Glyphosate Performance of Formulation, Additives and Mixing with other Herbicides, D. J. Turner (Weed Research Organization), The Herbicide Glyphosate, 1985, Ch. 15, pp. 221–140.

Primary Examiner—S. Mark Clardy
Attorney, Agent, or Firm—Howrey Simon Arnold & White LLP; Carter J. White

[57] ABSTRACT

The present invention concerns a new use of glyphosate or derivatives thereof for the increase of yield and/or quality of crop plants that are tolerant to glyphosate selected from sugar beet, fodder beet, corn, oilseed rape, and cotton.

9 Claims, No Drawings

USE OF N-(PHOSPHONOMETHYL) GLYCINE AND DERIVATIVES THEREOF

This application has been filed under 35 USC 371 as the national stage of international application PCT/EP97/01443, filed Mar. 21, 1997.

The present invention relates to a new use of glyphosate, or N-(phosphonomethyl)glycine, and derivatives thereof, such as salts and esters, as an agent for increasing the yield of crop plants that are tolerant to glyphosate.

Glyphosate is well known as an effective systemic, foliage active (post-emergent) non-selective herbicide. Glyphosate is known to act on various enzyme systems, thus interfering with the formation of amino acids and other endogenous chemicals in treated plants. Due to the relatively low water-solubility of the acid form, glyphosate is mostly sold in a salt form, like the mono-isopropylammonium salt, the ammonium salt, the sodium salt or others.

Well known formulated products comprise the active ingredient and a surfactant or a surfactant mixture and possibly other additives, like antifoam agents, antifreeze agents, dyes and other agents known in the art. Reference is also made to the book "The Herbicide Glyphosate", edited by E. Grossbard and D. Atkinson, Butterworth & Co, 1985.

U.S. Pat. No. 3,853,530 describes the use of N-phosphonomethylglycine and derivatives thereof to alter the natural growth or development of plants, like for defoliation and retardation of vegetative growth. In certain plants this retardation is said to lead to a shorter main stem and increased lateral branching. This alteration of the natural growth or development would produce smaller, bushier plants which often demonstrate increased resistance to drought and pest infestation. In the case of turf grasses, retardation of vegetative growth may also be highly desirable, thus enhancing root development to provide a dense, sturdier turf, and increasing the interval between mowings of lawns, golf courses and similar grassy areas. In many types of plants, such as silage crops, potatoes, sugar cane, beets, grapes, melons and fruit trees, the retardation of vegetative growth caused by glyphosate is said to result in an increase in the carbohydrate content of the plants at harvest. Obviously, these applications require sub-lethal doses, since otherwise the treated plants would be killed.

U.S. Pat. No. 3,988,142 more particularly relates to the use of N-phosphonomethylglycine and derivatives thereof to increase the carbohydrate deposition in plants, such as sugar cane. Again, the rates used are sub-lethal rates and are applied shortly before harvest.

In both instances mentioned above, it is believed that a non-lethal dose of glyphosate herbicide, i.e. a dose far below the doses normally used to combat the weed population in a crop field, causes a reduction or retardation of vegetative growth and the active material follows the normal pathway it follows when exerting its herbicidal action in the plants. In the case of U.S. Pat. No. 3,980,142, the retardation of vegetative growth is believed to permit more of the available carbohydrate in the plant to be converted to starch or sucrose, rather than being used as plant food for continued growth.

DE-3 200 486 relates to improving the productivity of crop plants by treating them with sub-lethal doses of phosphinothricin (glufosinate) which is also an efficient non-selective herbicide. Here as well, the inhibition of vegetative growth by sub-lethal doses of the herbicide is believed to cause an increase of carbohydrates in the plants or fruits thereof. DE-3 200 486 mentions glyphosate in a comparative example (Example II) which is intended to show that glufosinate has a better effect than glyphosate at the same rate.

EP-0 401 407 concerns a similar subject matter. It discloses the use of sub-lethal rates of non-selective herbicides, such as inter alia glyphosate and phosphinothricin, during the transition from the mass forming stage to the maturation stage of a plant, in order to increase the carbohydrate deposition in sugar or starch producing plants other than cane, such as sugar beets, potatoes or corn.

WO 95/05082 describes a method of increasing the yield of crops which are resistant to glutamine synthetase inhibitors, such as phosphinotricin, by treating the said crops with rates of that herbicide as used to combat the weeds in a crop field. This document further states that herbicides with a different mode of action don't have this effect or often show a negative effect on the crop yield.

Recent developments in gene technology have made it possible to genetically transform plants, more particularly crop plants, in order to render them tolerant to glyphosate or derivatives thereof. For instance EP-0 218 571 relates to a cloning or expression vector comprising a gene which encodes EPSPS polypeptide which when expressed in a plant cell confers glyphosate tolerance to plants regenerated from such cell. EP-0 293 358 further relates to the enhancement of the effectiveness of glyphosate-tolerant plants by producing mutant EPSP synthase enzymes which exhibit a lower affinity for glyphosate while maintaining catalytic activity. WO 92/00377 discloses genes encoding a glyphosate oxidoreductase enzyme. The genes are useful in producing transformed plants which degrade glyphosate herbicide and are tolerant to glyphosate herbicide. WO 92/04449 discloses genes encoding class II EPSPS enzymes, which are useful in producing transformed plants that are tolerant to glyphosate herbicide. Such crops can be maintained essentially weed free by application of glyphosate herbicide after crop emergence. Chemical Abstracts, vol. 124, N. 8, 1996, refers to an article in "Weeds" (1995) by B. H. Wells, entitled "Development of Glyphosate Tolerant Crops into the Market".

The author confirms that two approaches have been used to confer tolerance to commercial levels of glyphosate in several crops.

An article entitled Roundup Ready™ Sugar Beet by I. Brants et al., published early 1996 in the "Proceedings Of The International Symposium On Weed and Crop Resistance to Herbicides", a Symposium having taken place Apr. 3–6, 1995, shows that commercial Roundup® tolerance levels have been obtained in genetically modified sugar beet plants.

It has now been unexpectedly found that when treating crop land bearing a crop, such as beet crops, oilseed rape, or corn, that has been made tolerant to glyphosate herbicide, even with normally lethal rates of glyphosate herbicide or rates normally used to combat weeds, the crop yield is increased. This unexpected effect could not be expected from the above prior art, since in non-tolerant crops, the crop would be killed, and since phosphinothricin herbicides have a mode of action completely different from glyphosate herbicide.

Chemical Abstracts, vol 123, n° 21, 1995 publishes an abstract (Abstract N. 281158c) of an article by X. Delannay and others, which deals with the yield evaluation of a glyphosate-tolerant soybean line after treatment with glyphosate. The authors of the article conclude that the trends in the data generally suggested that no real differences existed, and that comparisons with standard herbicide checks reinforce the conclusion of overall yield safety of the glyphosate treatments, variability being understood to be due to unfavorable weather and/or soil conditions.

In Weeds (1995) mentioned earlier, B. H. Wells also notes that no significant yield reductions were seen after single or sequential broadcast applications of glyphosate at various crop stages. Lead lines of glyphosate tolerant cotton are said to have shown no yield reduction either after glyphosate applications. These evaluations were effected to confirm the performance of the genetic modification of the relevant crop plants as far as their tolerance to the relevant herbicide is concerned. No data is contained in this article and no disclosure or suggestion can be found for the possible yield increase of the crop after glyphosate application.

Although the earlier mentioned article by I. Brants et al. shows average root weight (%) data for three different lines of glyphosate tolerant sugar beet, characterised by three different transformation events, for several glyphosate treatments compared to a standard, the skilled person cannot derive beet yield increases from the data shown. The data have rightly been presented as tolerance testing data. The data shown is not indicative of any yield increase in sugar beets because tolerance evaluation is not effected in weed-free conditions and, hence, allows for weed competition in the standard plots. Further, as will be recognised by the skilled person, the data shown are very early data generated in small plots, with no replicates, at one location because of seed availability. Also, such early seeds still contained segregating seed material which resulted in irregular crop stands compared to the standard; as a consequence, the average root weight is computed per plant (not per unit area) and is compared to a standard grown under different conditions. The only conclusion a skilled person can draw from the above article is that three sugar beet lines have been found to show a level of tolerance that has potential for commercial development.

According to the invention, tests have shown yield increases (expressed per unit surface area) of glyphosate tolerant crops, such as beet crops, oilseed rape, corn or cotton, treated with glyphosate herbicide of up to about 50% when compared to the same crop that has not been treated with glyphosate herbicide. The yield increase is not believed to be due simply to less competition between weeds and crops as a consequence of the glyphosate herbicide applications, because the effect has been noticed on crops allowed to grow under essentially weed-free conditions. Also no growth regulation effect as understood in the prior art of record has been noticed: No temporary retardation of growth has been noticed or any other temporary alteration of the natural growth or development of the crop plant.

The present invention is therefore concerned with the use of glyphosate or derivatives thereof for the yield increase of glyphosate tolerant crops.

Preferably, glyphosate is applied at the usual lethal doses for controlling weed population in order to simultaneously kill the weeds. Glyphosate herbicide can be applied once or in several successive treatments. The applied rates are generally comprised in the range of between 0,2 and 6.0 kg acid equivalent/ha, depending on the climatic conditions, the season, the weed infestation, stage of the weed plants, and depending on the crop and other parameters known by the person skilled in the art.

Glyphosate herbicide may be applied in its acid form or as a derivative thereof, preferably a salt, such as the mono isopropylammonium salt, the sodium salt, or ammonium salt or mixtures thereof. Other salts of glyphosate wherein the cation is not in itself herbicidally active or phytotoxic may also be used.

The yield increasing effect of glyphosate herbicide treatment has been noticed on glyphosate tolerant crops selected from beets such as sugar beet or fodder beet, corn, oil seed rape and cotton, independently of the technique used for causing glyphosate tolerance.

The effect is particularly marked on glyphosate tolerant sugar beets and fodder beets.

Glyphosate herbicide can for instance be applied in its acid form or in the form of derivatives thereof, as a water-soluble or dispersible granule, as a water-soluble concentrate diluted in the spray water, or in the form of other formulation types, such as emulsions, encapsulated active ingredient and others.

Glyphosate herbicide may be applied in one application or sequential applications, at different plant growth stages. The effect of the glyphosate herbicide treatment on glyphosate tolerant crops has shown to be the most significant when treatment is applied in the growth stage of the relevant plants.

Such formulation adjuvants may be found in "McCutcheon's Emulsifiers and Detergents", and may advantageously be selected from amines, such as ethoxylated alkyl amines, particularly tallow amines, cocoamines, surfactants sold under the tradename Ethomeen, amine oxides, such as surfactants sold under the tradename Empigen OB;

quaternary ammonium salts, such as ethoxylated and/or propoxylated quaternary ammonium salts, more particularly surfactants sold under the tradenames Ethoquad, Emcol CC and Dodigen;

alkylpolyglycoside, alkylglycoside, glucose- and sucrose-esters.

Most preferred are quaternary ammonium salts, such as defined in EP-0 441 764, possibly in admixture with a wetting agent, most preferably alkoxylated sorbitan ester. This type of surfactant or surfactant mix shows no significant phytotoxic effect on the crop plants and is preferred for its environmentally friendly characteristics.

Quaternary ammonium salts of particular interest are trimethyl ethoxypolyoxypropyl ammonium chlorides.

EXAMPLE 1

Sugar beet plants genetically modified according to the technology disclosed in EP-0 218 571 to render them tolerant to glyphosate were planted according to good agronomical practices at 4.5 cm interplant distance within a row and thinned manually to ensure normal crop stand, according to a randomized block design; plot size: 2.7×6 m; 6 rows per plot with an inter-row distance of 0.45 m. Four replications were used for each test.

The test plots were kept essentially weed free: by pre-emergent herbicide applications, if so required and specified, by post-emergent glyphosate treatments applied as specified below or standard officially accepted beet treatments (for comparison purposes)

The following treatments were applied
N.1 Standard sugar beet herbicide
N.2 Standard sugar beet herbicide at double rate
N.3 3×720 g a.e/ha of formulated glyphosate
N.4 3×1080 g a.e/ha of formulated glyphosate
N.5 3×1440 g a.e/ha of formulated glyphosate
N.6 2×2160 g a.e/ha of formulated glyphosate.

If three successive applications of glyphosate herbicide are effected, the first one is carried out at the 2–4 leaf stage of the crop plants; the second one is carried out at the 6–8 leaf stage of the crop plants; and the third one is carried out at the 10–12 leaf stage of the crop plants, but before canopy closure.

If two successive applications are carried out than the first one is carried out at the 2–4 leaf stage and the second one is carried out at the 10–12 leaf stage of the crop plants.

The formulation of glyphosate herbicide comprised 360 g glyphosate a.e./l as the isopropylammonium salt, and 180 g/l surfactant composed of trimethyl ethoxypolyoxypropyl(8) ammonium chloride and ethoxylated (20) sorbitan ester (80:20). The glyphosate formulation was applied at a water volume of 200 l/ha at a 2 bar pressure.

The fresh root weight was measured at harvest. The fresh root weight after Standard treatment N.1 was considered as 100% yield and the measured fresh root weights were related to the result of Standard treatment N.1.

TABLE I.a

| Trt | % yield (fresh root weight per hectare) |
|---|---|
| 1* | 100 |
| 2* | 96 |
| 3 | 108 |
| 4 | 108 |
| 5 | 110 |
| 6 | 113 |

*The standard treatment comprised three applications
| Herbasan | 1.0 L/ha | 1.0 L/ha | 1.0 L/ha |
| Ethosan | 0.1 L/ha | 0.2 L/ha | 0.2 L/ha |
| Goltix | 1.0 Kg/ha | 1.0 Kg/ha | 1.0 Kg/ha |
| Renol S | 0.3 L/ha | 0.3 L/ha | 0.3 L/ha |

TABLE I.b

| Trt | % Yield (fresh root weight per hectare) |
|---|---|
| 1* | 100 |
| 2* | 102 |
| 3 | 110 |
| 4 | 113 |
| 5 | 117 |
| 6 | 113 |

*The standard treatment comprised three applications
| Goltix | 1.7 Kg/ha | 0.75 Kg/ha | 1.0 Kg/ha |
| Actipron | 1.7 L/ha | | |
| Betanal E | | 2.0 L/ha | |
| Venzar | | 0.4 L/ha | |
| Goltix | | | |
| Betanal Prog. | | | 2.0 L/ha |

TABLE I.c

| Trt | % Yield (fresh root weight per hectare) |
|---|---|
| 1* | 100 |
| 2* | — |
| 3 | 129 |
| 4 | 156 |
| 5 | 136 |
| 6 | 132 |

*Standard treatment comprised a pre-emergent application and two post-emergent applications of officially accepted sugar beet herbicides, as follows:
| Goltix | 3 Kg/ha | 0.5 Kg/ha | 0.5 Kg/ha |
| Pyramin DF | 2 Kg/ha | | |
| Betanal P | | 1.0 Kg/ha | 1.0 Kg/ha |
| Stratos | | | 1.0 Kg/ha |

EXAMPLE 2

The same tests were repeated with a glyphosate tolerant fodder beet (genetically transformed according to the same technology).

TABLE II.a

| Trt | % Yield (fresh root weight per hectare) |
|---|---|
| 1* | 100 |
| 2* | 101 |
| 3 | 108 |
| 4 | 107 |
| 5 | 110 |
| 6 | 111 |

The Standard (*) of this test comprised three applications:
| Herbasan | 1.0 L/ha | 1.0 L/ha | 1.0 L/ha |
| Ethosan | 0.1 L/ha | 0.2 L/ha | 0.2 L/ha |
| Goltix | 1.0 Kg/ha | 1.0 Kg/ha | 1.0 Kg/ha |
| Renol S | 0.3 L/ha | 0.3 L/ha | 0.3 L/ha |

The same test was repeated with the same line as above, except that a pre-emergent herbicide treatment has been applied over all plots, which consisted of 1 kg/ha of Goltix (tradename) and 3 l/ha of Betanal E (tradename).

TABLE II.b

| Trt | % Yield (fresh root weight per hectare) |
|---|---|
| 1* | 100 |
| 2* | 100 |
| 3 | 108 |
| 4 | 110 |
| 5 | 113 |
| 6 | 110 |

*The standard of this test comprised one application:
| Goltix | 1 Kg/ha |
| Betanal E | 3 L/ha |

EXAMPLE 3

For this experiment, essentially the same protocol was followed, as in Examples 1 and 2.

Glyphosate tolerant sugar beet plants were planted early May 1995 according to good agricultural practice. The plots were kept essentially weed free by manual cleaning (untreated) or by applications of glyphosate herbicide, as appropriate. Glyphosate was applied as a formulation of the isopropylammonium salt of glyphosate comprising 360 g/l acid equivalent and 180 g/l of surfactant (trimethylethoxypolyoxypropyl (8) ammonium chloride (80) with ethoxylated (20) sorbitan ester (20)).

T1=2–4 leaf stage (approximately 30 DAP—Days After Planting)
T2=8–10 leaf stage (approximately 50 DAP)
T3=14–18 leaf stage (approximately 65 DAP)

The Table IV below shows the measured average fresh weight (in g) of the roots per plant, 180 DAP, for several rates of glyphosate formulation as specified above.

TABLE III

| T1 | T2 | T3 | 180 DAP g |
|---|---|---|---|
| Untreated | Untreated | Untreated | 1420 |
| 2 | 2 | 2 l | 1717 |
| 3 | 0 | 3 l | 1538 |
| 6 | 0 | 6 l | 1885 |
| 4 | 0 | 4 l | 1904 |

This experiment clearly shows the increase in fresh root weight at harvest, after several glyphosate applications. There also is a trend of increased yield as a function of the rates of glyphosate applied.

The increased yield is also translated into a corresponding increased dry weight of the plant at harvest.

EXAMPLE 4

The purpose of this experiment is to compare transgenic sugar beets that have been sprayed with a formulation of glyphosate herbicide, and transgenic sugar beets that have not been treated with such a herbicidal formulation, from the point of view of beet quality (content of sugar, invert sugar, potassium, sodium, amino-nitrogen of the roots; nutrients of beet roots and top samples, such as % dry matter, crude fibre and toxins content).

Sugar beets are mainly used in the sugar industry for production of white sugar, pulp and molasses. The technological value of the beet for this purpose is commonly evaluated by analysing their content of sugar, potassium, sodium and amino-nitrogen. Concerning toxicants in beets, the saponins are monitored.

Preparation of samples

After harvest, the roots were kept between 0° C. and 10° C., and the top samples were frozen at less than −20° C.

The preparation of beet into brei is done by a semi-automatic treatment, where the beet is sliced in a beet saw to produce brei. After the brei was homogenized, 1 sub-sample was used after extraction to analyze for polarization, invert sugar, Na, K and Amino-N, and another subsample was dried and used for nutrients. A third part of the same brei sample was frozen for toxicants. The extraction of beet brei was done with demineralized water to which was added a tablet of aluminum sulfate for clarifying, and transferred to the automatic Venema digestion and filtration plant. Preparation of large beet top was done by dividing them horizontal into equal sub-samples.

Analytical methods

Dry Matter—Oven method (EF 71/393/E0F; L279/7 p. 858–61 20/12–71)

Root

After the root is processed into brei, the brei sample is placed in oven at 95° C. and dried for 24 hours (to constant weight).

Top

The sample is placed in oven at 95° C. and dried for up to 72 hours, depending on the size of the sample, to constant weight.

For both root and top the loss in weight is quantified and calculated as percent dry matter.

Crude Fibre—Weende method (EF L 344/36–37 26/11–92 modified):

The sample is treated successively with boiling solutions of sulfuric acid and potassium hydroxide of specified concentrations. The residue is separated by filtration on Gosch crucible with glass wool, washed, dried, weighed and incinerated in a muffle oven at 550° C. in 3 hours. The loss of weight from incinerating is quantified gravimetrically and calculated as percent Crude Fibre of the sample.

Toxins: saponins—HPLC method (Hilmer Sorensen, KVL 1991, modified by DC)

The method is based on an acid hydrolysis of beet saponins. The liberated oleanolic acid is extracted with dichlormethane. After evaporation of water from the sample the remanence is dissolved in methanol. The oleanolic acid is estimated by HPLC at reverse phase with acetonitrile/water as eluent and determined at 210 nm on UV-detector.

Sugar content of beet extract—Polarization (Pol) (ICUMSA, Sugar Analysis 1979, Proc. 1990)

The beet extract, clarified with aluminum sulfate, is determined on a polarimeter type PROPOL, which is based on determination of a ratio of optical rotation. The optical rotation is measured at 546 nm in a 70 mm long tube and converted to ° Z (Pol %) or g/100 g root.

Amino-Nitrogen of beet extract—SMAIIC Analyzer (ICUMSA, Sugar Analysis 1979 modified):

The beet extract, clarified with aluminum sulfate, is determined on calorimeter at 570 nm, after a color reaction with ninhydrin.

Potassium and Sodium of beet extract—SMAIIC Analyzer (Technicon, Tech. Publ. THO-0160-10)

The beet extract, clarified with aluminum sulfate, is determined on Flame Photometer IV, where the intensity of light energies emitted by potassium and sodium in the flame is measured at respectively 589 nm and 768 nm. The sample is diluted with lithium sulfate, where lithium is used as internal standard to balance the signal from the Flame Photometer.

Invert sugar of beet extract—SMAIIC Analyzer (Technicon, Tech. Publ. THO-0160-10)

The beet extract, clarified with aluminum sulfate, is determined on colorimeter at 560 nm, after reaction with copper sulfate neocuproin hydrochlorid reagent.

Glyphosate tolerant sugar beet plants, genetically transformed according to the technology disclosed in EP-0 218

571 for tolerance to glyphosate herbicide, were grown at 6 different locations (Italy, Spain, Belgium, Denmark, France, UK).

The type of varieties grown are depending on local requirements. The material varies in many characters, one important character is the sugar content estimated by polarization (Pol). The sugar beet can be divided into subgroups: E-type, N-type and Z-type. E-type is low in Pol, Z-type is high in Pol and N-type in between E and Z. Varieties grown in Northern Europe can be characterized as being E-N, N or N-Z types. The material used in this Example falls into the N group.

The sugar beets were planted according to local good agronomical practices, manually thinned to ensure normal crop stand. At least one replicate per test was used.

The plots were kept essentially weed free by application of:

glyphosate herbicide on the test plots standard beet selective herbicide treatments (according to locations) on the control plots; except in Denmark, Italy, where no other herbicide than glyphosate was considered necessary to maintain weed free conditions.

The formulation of glyphosate herbicide is the same as the one used in Example 1. The herbicidal glyphosate formulation was applied as follows

| preemergent | 2.5 l/ha |
|---|---|
| 2–4 true leaf stage of beets | 2 l/ha |
| 6–8 true leaf stage of beets | 2 l/ha |
| 12–14 true leaf stage (canopy closure) | 2 l/ha |

The selective herbicide rates applied are as follows

Spain:

| 3.55 kg/ha Goltix WG | (metamitron) preemergent. |
|---|---|

Belgium:

| 2 l/ha Gramoxone (paraquat 200) | preplanting |
|---|---|
| 3 l/ha Pyramin FL (chloridazone 430) | 1 week after planting |
| 0.5 l/ha Betanal (Phenmediphame 150) | 3 weeks after planting |
| 0.5 l/ha Goltix (metamitron 70% WP) | 3 weeks after planting |
| 0.5 l/ha Tramat (Ethofumesate 200) | 3 weeks after planting |
| 0.75 l/ha Goltix | 5 weeks after planting |
| 0.75 l/ha Vegelux (Mineral oil 40) | 5 weeks after planting |
| 0.75 l/ha Tramat | 5 weeks after planting |
| 0.75 l/ha Goltix | 6 weeks after planting |
| 0.75 l/ha Vegelux | 6 weeks after planting |
| 0.17 l/ha Fusilade | 6 weeks after planting |
| 0.75 l/ha Betanal | 6 weeks after planting |
| 0.75 l/ha Tramat | 9 weeks after planting |
| 0.75 l/ha Betanal | 9 weeks after planting |
| 0.75 l/ha Goltix | 9 weeks after planting |
| 0.75 l/ha Vegelux | 9 weeks after planting |

France:

| 0.75 l/ha Goltix WP (metamitron) | 1 day after planting |
|---|---|
| 0.75 l/ha Goltix WP | 2 weeks after planting |
| 0.75 l/ha Betanal (Phenmediphame 150) | 2 weeks after planting |
| 0.75 l/ha Tramat (Ethofumesate 200) | 2 weeks after planting |

U.K.:

| 1.0 l/ha Laser (cycloxydim) | 5 weeks after planting |
|---|---|

The analytical results were collected and the averages are reproduced in the table below, all countries having an equivalent weight in the computation of the averages.

| Plant part | Analysed unit | Trt/Unt | Sugar beet |
|---|---|---|---|
| brei | dry matter (DM) | Trt | 21.309 |
|  | g/100 g root | Unt | 20.444 |
| root | Invert sugar | Trt | 1.011 |
|  | mmol/100 g root | Unt | 1.755 |
|  | potassium | Trt | 5.162 |
|  | mmol/100 g root | Unt | 5.286 |
|  | NH2N | Trt | 2.470 |
|  | mmol/100 g root | Unt | 2.878 |
|  | sodium | Trt | 1.118 |
|  | mmol/100 g root | Unt | 1.769 |
|  | Pol | Trt | 15.610 |
|  | g/100 g root | Unt | 14.478 |
| top | dry matter | Trt | 14.724 |
|  | g/100 g top | Unt | 13.996 |

Trt: sprayed with glyphosate herbicide
Unt: not sprayed with glyphosate herbicide
DM: dry matter.

The data show that sugar beets treated with glyphosate herbicide present a significantly higher sugar content with reduced sodium, potassium, amino-nitrogen and invert sugar in the root. The dry matter of root and top is also increased. More detailed data suggest that the leaves of glyphosate treated sugar beets show a higher fiber content.

Correlating the results of this Example with the results of the previous Examples, it appears that the yield increase evaluated earlier in weight per hectare also reflects as an increase of dry matter, fiber, and sugar content in the harvested material.

EXAMPLE 5

Sugar beet and fodder beet plants genetically modified according to the technology disclosed in EP-0 218 571 to render them tolerant to glyphosate were planted at different locations according to good agronomical practices at 4.5 cm interplant distance within a row and thinned manually to ensure normal crop stand, according to a randomized block design; plot size: 2.7×7 m; 6 rows per plot with an inter-row distance of 0.45 m. Four replications were used for each test.

The test plots were kept essentially weed free by standard pre-emergent herbicide applications over the whole area, and than by handweeding and, as appropriate by post-emergent glyphosate treatments applied as specified below.

The following treatments were applied
Hand weeding only
3×720 g a.e/ha of formulated glyphosate
3×1080 g a.e/ha of formulated glyphosate
3×1440 g a.e/ha of formulated glyphosate
2×2160 g a.e/ha of formulated glyphosate.

If three successive applications of glyphosate herbicide are effected, the first one is carried out at the 2–4 leaf stage of the crop plants; the second one is carried out at the 6–8 leaf stage of the crop plants; and the third one is carried out at the 10–12 leaf stage of the crop plants, but before canopy closure.

If two successive applications are carried out than the first one is performed at the 2–4 leaf stage and the second one at the 10–12 leaf stage of the crop plants.

The formulation of glyphosate herbicide comprised 360 g glyphosate a.e./l as the isopropylammonium salt, and 180 g/l surfactant composed of trimethyl ethoxypolyoxypropyl (8) ammonium chloride and ethoxylated (20) sorbitan ester (80:20). The glyphosate formulation was applied at a water volume of 200 l/ha at a 2 bar pressure.

The fresh root weight was measured at harvest. The fresh root weight of the solely handweeded plots was considered as 100% yield and the measured fresh root weights after glyphosate treatments were related to the result of the handweeded plots.

TABLE V

| Trt | % yield (fresh root weight) | |
| --- | --- | --- |
| | Sugar beet | fodder beet |
| handweeded | 100% | 100% |
| 3 × 720 g a.e. | 101 | 105 |
| 3 × 1080 g a.e. | 98 | 106 |
| 3 × 1140 g a.e. | 115 | 108 |
| 2 × 2160 g a.e. | 107 | 102 |

EXAMPLE 6

For this field trial, winter oilseed rape plants with existing genetic background, genetically modified for exhibiting glyphosate herbicide tolerance (according to the combined technique of EPSPS expression and glyphosate oxidoreductase expression), were planted mid September 1995, according to good agronomical practices at 4 kg seeds/ha corresponding to approximately 100 plants per m2 (normal crop stand), according to a randomized block design; plot size: 3×7 m, 0,14 m interrow distance; 4 replications per test.

The plots were kept essentially weedfree : by a standard preemergent herbicide application over the whole area, i.e. 1,5 l Butisan (metazachlor) one day after drilling and 1 l in addition over the standard plots; and by glyphosate treatments applied as specified below The glyphosate treatments were applied in the autumn at a plant growth stage of B4-B5; the same formulation as the one used in Example 1 was applied.

Harvest occurred early August and yield was evaluated and expressed in ton/ha grains (at 9% humidity). The Table VI shows the measured yields in % of the yield of the standard plot.

TABLE VI

| Yield | |
| --- | --- |
| Standard | 100 |
| 1080 g a.e./ha | 104.5 |

EXAMPLE 7

This field test was performed similarly to the test of the previous Example, except that in this Example spring oilseed rape plants were sown (mid April 1996). Such plants having known genetic background were rendered tolerant to glyphosate herbicide by the combined technique as mentioned in Example 6.

The plots were kept weed free by application of 1,5 l/ha Butisan over the whole area, and handweeding for the standard plot, and glyphosate herbicide for the remaining plots. The same glyphosate formulation was applied approximately 1 month after planting, i.e. plant growth stage B3-B4. Harvest occurred mid August.

Table VII below shows the yield data (measured and expressed as in Example 6) in % yield of the standard plots.

TABLE VII

| Yield | |
| --- | --- |
| Standard | 100 |
| 720 g a.e./ha | 120 |
| 1080 g a.e./ha | 112 |

EXAMPLE 8

Further field trials were carried out in Italy to evaluate the yield enhancement of glyphosate tolerant corn crops after glyphosate herbicide application(s) Known corn plants genetically modified for glyphosate tolerance according to the combined techniques of EPSPS and of glyphosate oxidoreductase expression were planted and grown according to good agronomical practice at approx. 62,000 plants/ha (approx. 4.7 seeds/m) in plots of 3×9 m, with four 9 m rows of plants each, in a complete randomized block design with four replicates, and then manually thinned to ensure normal crop stand and same number of plants in all plots. The whole area comprising standard plots and test plots was treated by a preemergent herbicide (Lasso Micromix) at a rate of 6 l/ha (i.e. 2016 g alachlor and 864 g terbuthylazine) . Standard plots were kept weedfree by handweeding, if required, and the test plots by treatment with the same glyphosate formulation as in Example 1, at several rates and plant growth stages. Only both the central rows were harvested on a median length of 7 m. The yield was measured in ton grains per hectare expressed at 15% humidity, and is expressed in the Tables as % yield of standard (STD).

TABLE XIII a

| % Yield/glyphosate treatment at 3–4 leave stage | | |
| --- | --- | --- |
| | Transformation event 1 | Transformation event 2 |
| STD | 100 | 100 |
| 720 g a.e./ha glyphosate | 106 | 103 |
| 1800 g a.e./ha | 107 | 107 |

TABLE XIII b

Yield/glyphosate treatment at 5–6 leave stage

|  | Transformation event 1 | Transformation event 2 |
|---|---|---|
| STD | 100 | 100 |
| 720 g a.e./ha glyphosate | 114 | 105 |
| 1080 g a.e/ha | 109 | 108 |
| 1440 g a.e./ha | 109 | 105 |
| 1800 g a.e./ha | 111 | 102 |

EXAMPLE 9

A further field test was carried out according to the same protocol as in Example 1, in order to evaluate the effect of different formulations of glyphosate herbicide on the yield enhancement. The transgenic crop plants received three glyphosate herbicide treatments of 720 g a.e./ha and of 1080 g a.e./ha, respectively.

TABLE IX

|  | % yield - fresh root weight | |
|---|---|---|
|  | 3 × 720 g a.e. | 3 × 1080 g a.e. |
| Roundup ® | 100 | 100 |
| Granular formulation | 101.4 | 100.2 |
| Liquid formulation | 104.2 | 102 |

Roundup ® :

-glyphosate isopropylammonium salt at 360 g a.e./l
-ethoxylated tallow amine surfactant at 180 g/l
Solid formulation:

-glyphosate sodium at 430 g a.e./kg
-trimethyl ethoxypolyoxypropyl (8) ammonium chloride at 160 g/kg
-ammonium sulfate at 330 g/kg Liquid formulation: the same as used in Example 1.

This Example shows a tendency towards improved performance of the formulation comprising environmentally friendly surfactant as defined.

EXAMPLE 10

A similar procedure as the one described in Example 7 (spring oilseed rape) was followed in this Example in order to evaluate the effect of different formulations of glyphosate herbicide. The test plots in this trial were of 1.5×10 m.

TABLE X

Yield in ton/ha grains at 9% humidity

|  | % YIELD | | | |
|---|---|---|---|---|
| l/ha | 1 | 2 | 3 | 4 |
| Roundup ® | 100 | 100 | 100 | 100 |
| Granular form. | 101 | 103 | 109 | — |
| Liquid form. | 103 | 101 | 110 | 108 |

The yield obtained after Roundup ® treatments have been considered as 100%.

This example further confirms the superiority of the formulation used in example 7.

What is claimed is:

1. A method of increasing the yield of glyphosate tolerant crops selected from the group consisting of: sugar beet, fodder beet, corn, oilseed rape and cotton;

the method comprising: treating said crop with an effective amount of glyphosate or a derivative thereof.

2. The method of claim 1, wherein the glyphosate or derivative thereof is applied at a usually lethal dose between 0.18 and 5.3 lb. acid equivalents/acre (0.2 and 6.0 kg acid equivalents/ha).

3. The method of either claim 1 or 2 wherein the glyphosate or derivative thereof is applied in a single treatment or in successive treatments.

4. The method of claim 3 wherein the glyphosate derivative is a glyphosate salt or a mixture of glyphosate salts selected from the group consisting of:

mono-isopropylammonium glyphosate, ammonium glyphosate, and sodium glyphosate.

5. The method of claim 3 wherein the glyphosphate or derivative thereof is used in a formulation comprising: an adjuvant selected from the group consisting of:

amines, ethoxylated alkyl amines, tallow amines, cocoamines, amine oxides, quaternary ammonium salts, ethoxylated quaternary ammonium salts, propoxylated quaternary ammonium salts, alkylpolyglycoside, alkylglycoside, glucose-esters, sucrose- esters, and ethoxylated polypropoxylated quaternary ammonium surfactants.

6. The method of claim 3 wherein glyphosate or a derivative thereof is used to increase the yield and/or quality of a sugar or fodder beet.

7. The method of claim 3 wherein the crop contains a gene which encodes EPSPS polypeptide.

8. The method of claim 3 wherein the crop contains a gene encoding a glyphosate oxidoreductase enzyme.

9. The method of claim 3 wherein the crop contains a gene encoding a class II EPSPS enzyme.

* * * * *

UNITED STATES PATENT AND TRADEMARK OFFICE
CERTIFICATE OF CORRECTION

PATENT NO. : 6,083,878
DATED : July 4, 2000
INVENTOR(S) : Ivo O. Brants and William Graham It is certified that error appears in the above-identified patent and that said Letters Patent is hereby corrected as shown below:

On the Title page of the Patent beside number 73, please delete "Monsanto Company" and insert -- Monsanto Europe S.A. --

In Colum 1, line 59, delete "3,980,142" and insert -- 3,988,142 --

Signed and Sealed this

Thirty-first Day of October, 2000

Attest:

Q. TODD DICKINSON

Attesting Officer

Director of Patents and Trademarks